United States Patent [19]

Ichikawa et al.

[11] Patent Number: 5,540,683

[45] Date of Patent: Jul. 30, 1996

[54] HIGH FREQUENCY CAUTERIZING APPARATUS

[75] Inventors: Yoshito Ichikawa, Saitama-ken; Kazuya Hijii, Tokyo, both of Japan

[73] Assignee: Olympus Optical Co., Ltd., Tokyo, Japan

[21] Appl. No.: 273,910

[22] Filed: Jul. 12, 1994

[30] Foreign Application Priority Data

Nov. 8, 1993 [JP] Japan ..................................... 5-278460

[51] Int. Cl.⁶ .................................................. A61B 17/36
[52] U.S. Cl. .................................. 606/40; 606/38; 606/46; 606/49; 606/50
[58] Field of Search .................................... 606/1, 32–35, 606/38–42, 45–52; 604/20, 21

[56] References Cited

U.S. PATENT DOCUMENTS

| | | |
|---|---|---|
| 4,532,924 | 8/1985 | Auth et al. . |
| 4,580,557 | 4/1986 | Hertzmann .............................. 606/12 |
| 4,936,842 | 6/1990 | D'Amelio .............................. 606/42 |
| 4,938,761 | 7/1990 | Ensslin . |
| 5,108,391 | 4/1992 | Flachenecker et al. . |
| 5,152,762 | 10/1992 | McElhenney . |
| 5,207,675 | 5/1993 | Canady ..................................... 606/46 |
| 5,234,427 | 8/1993 | Ohtomo .................................... 606/42 |
| 5,267,997 | 12/1993 | Farin et al. ............................... 606/38 |
| 5,383,874 | 1/1995 | Jackson et al. ........................... 606/41 |

FOREIGN PATENT DOCUMENTS

| | | |
|---|---|---|
| 2-246964 | 10/1990 | Japan . |
| 4-75510 | 7/1992 | Japan . |

*Primary Examiner*—Angela D. Sykes
*Assistant Examiner*—Michael Peffley
*Attorney, Agent, or Firm*—Frishauf, Holtz, Goodman, Langer & Chick

[57] ABSTRACT

A high-frequency cauterizing apparatus comprises a high-frequency power supply device, having a plurality of high-frequency output modes, for generating a high-frequency current, at least one medical treatment instrument to be connected to the high-frequency power supply device, a detector for detecting connection of the medical treatment instrument to the high-frequency power supply device, a control signal generator for identifying the type of the medical treatment instrument on the basis of a detection signal from the detector and generating a control signal, and a controller for controlling a high-frequency output from the high-frequency power supply device on the basis of the control signal generated from the control signal generator.

18 Claims, 10 Drawing Sheets

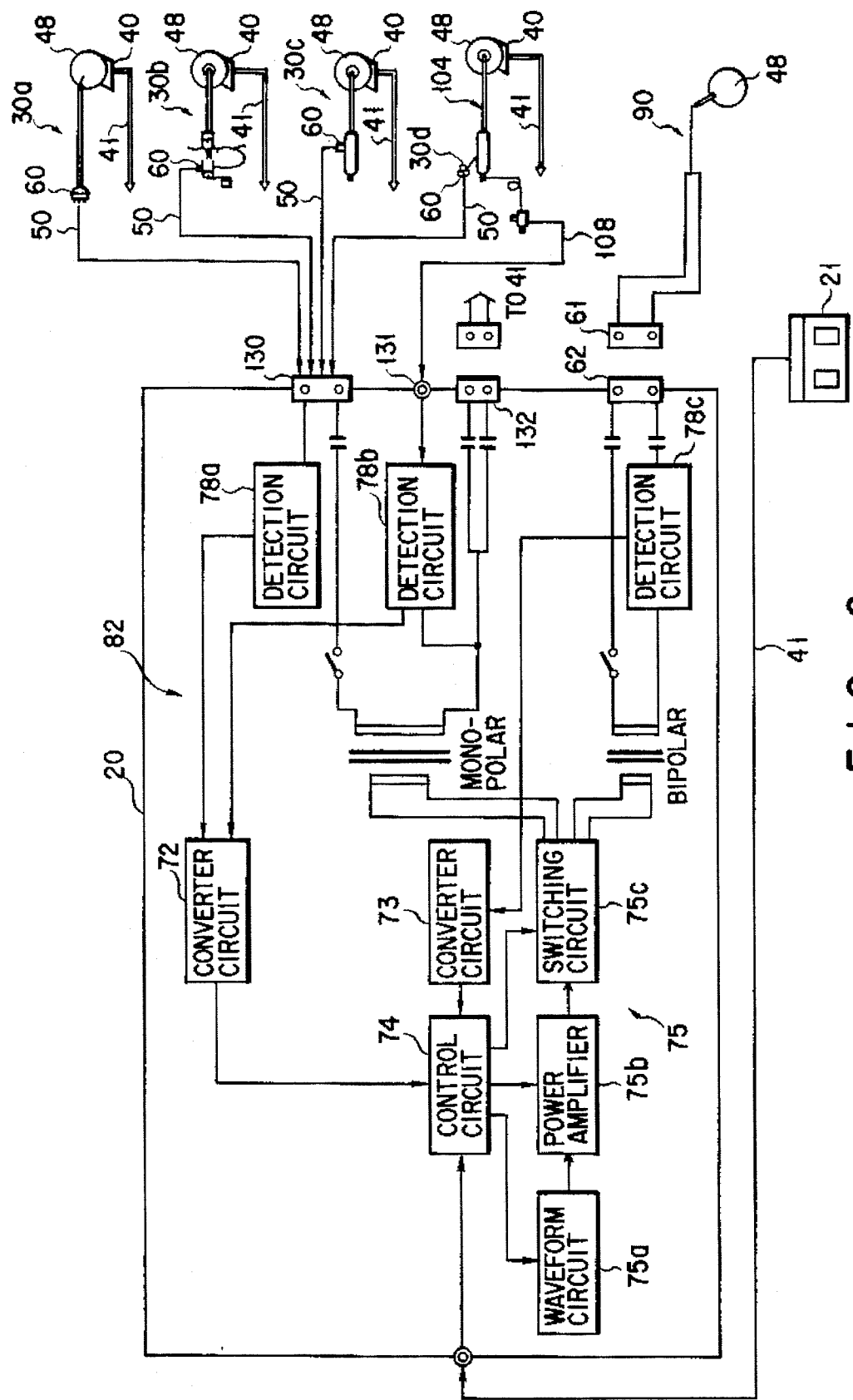
F I G. 6

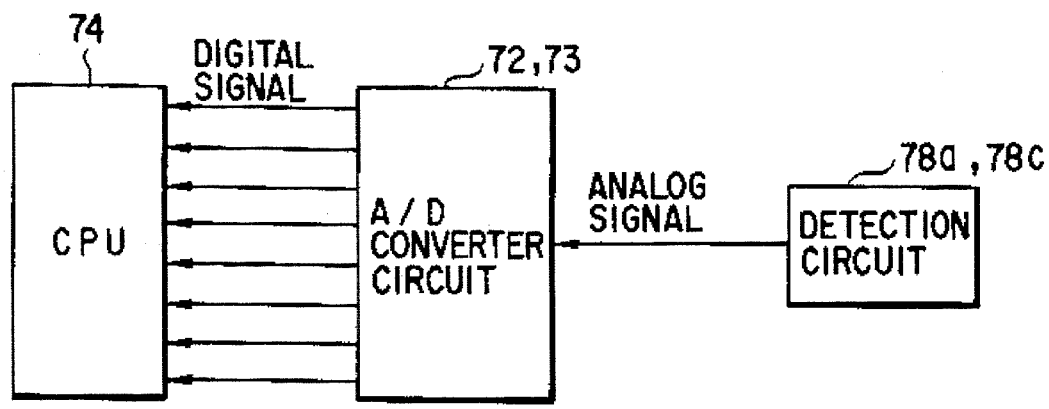
F I G. 7
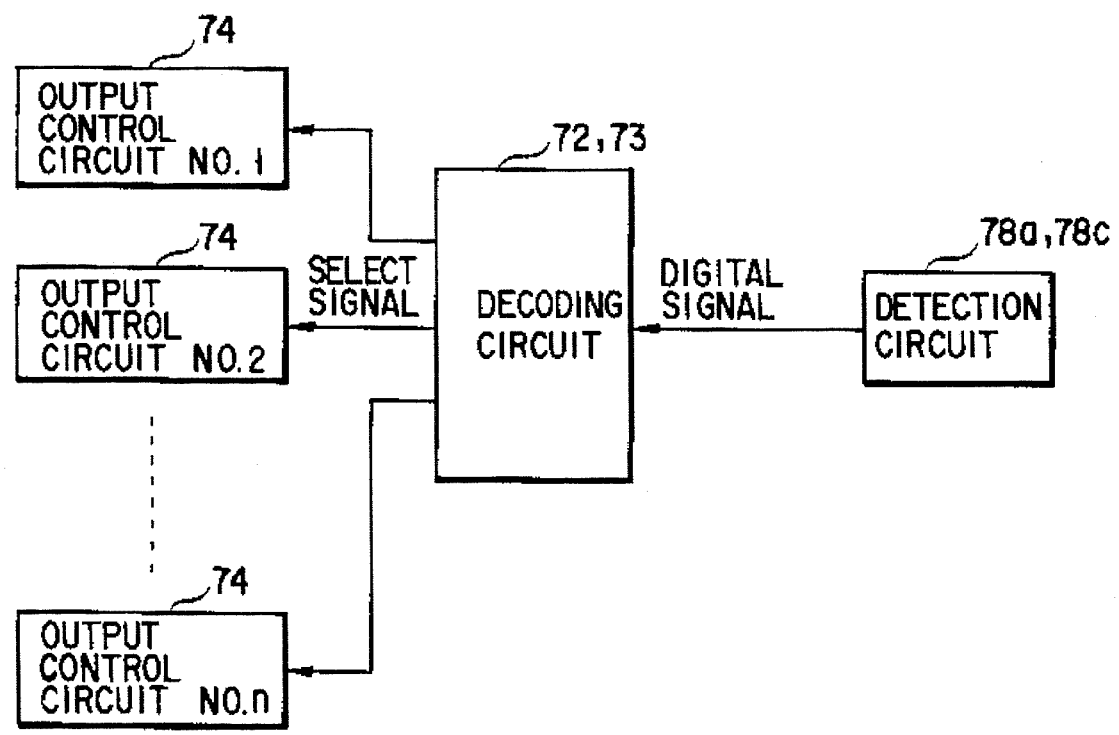
F I G. 8

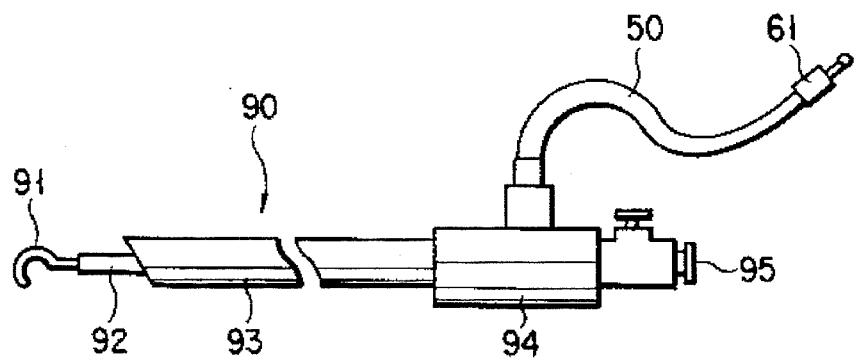
F I G. 12
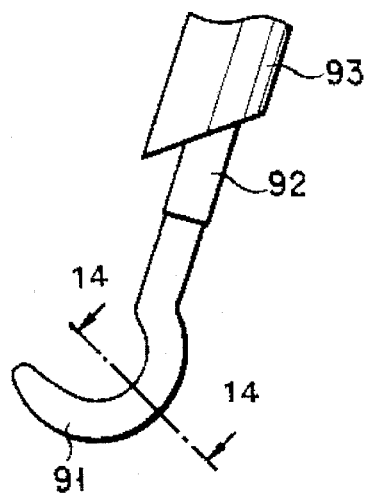
F I G. 13
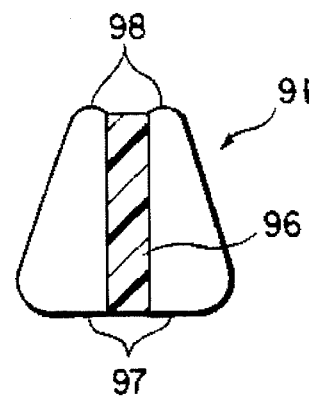
F I G. 14

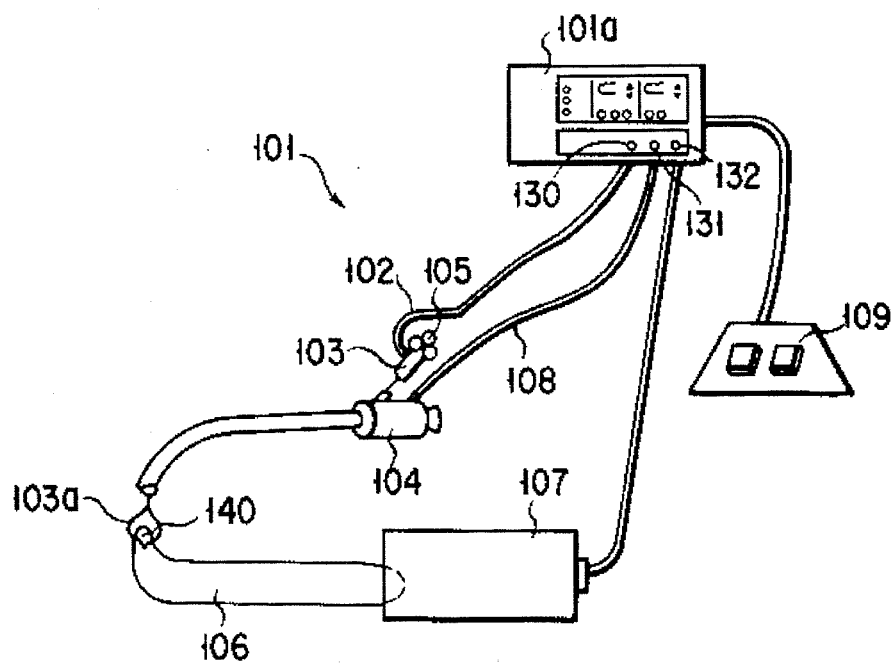
F I G. 15
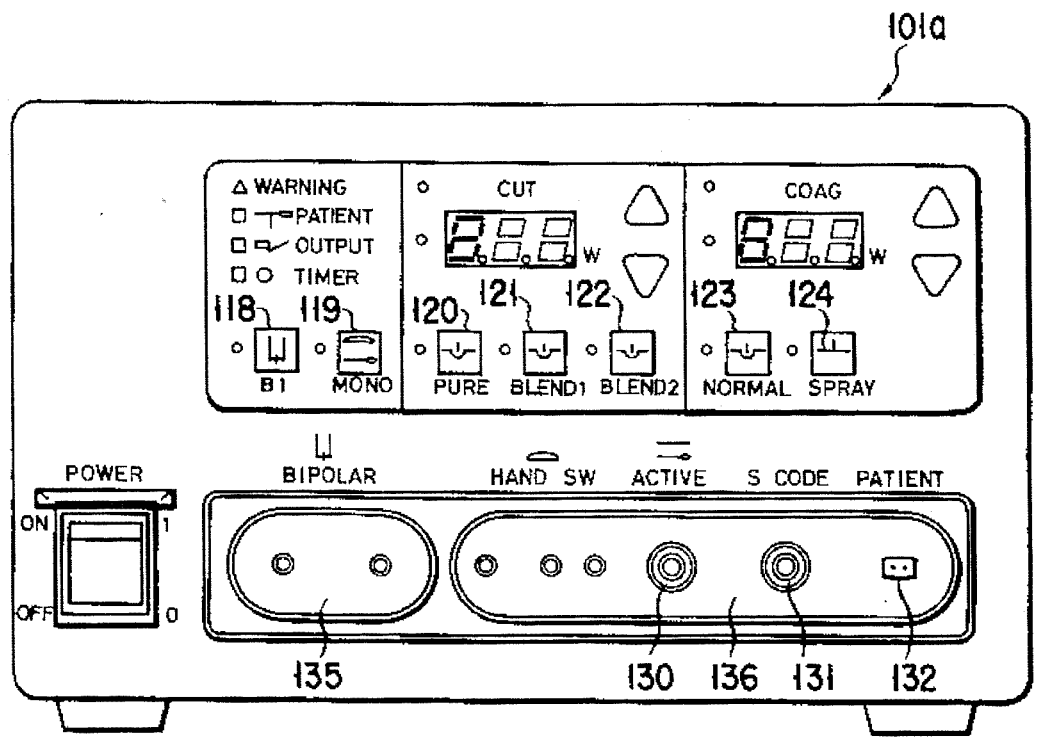
F I G. 16

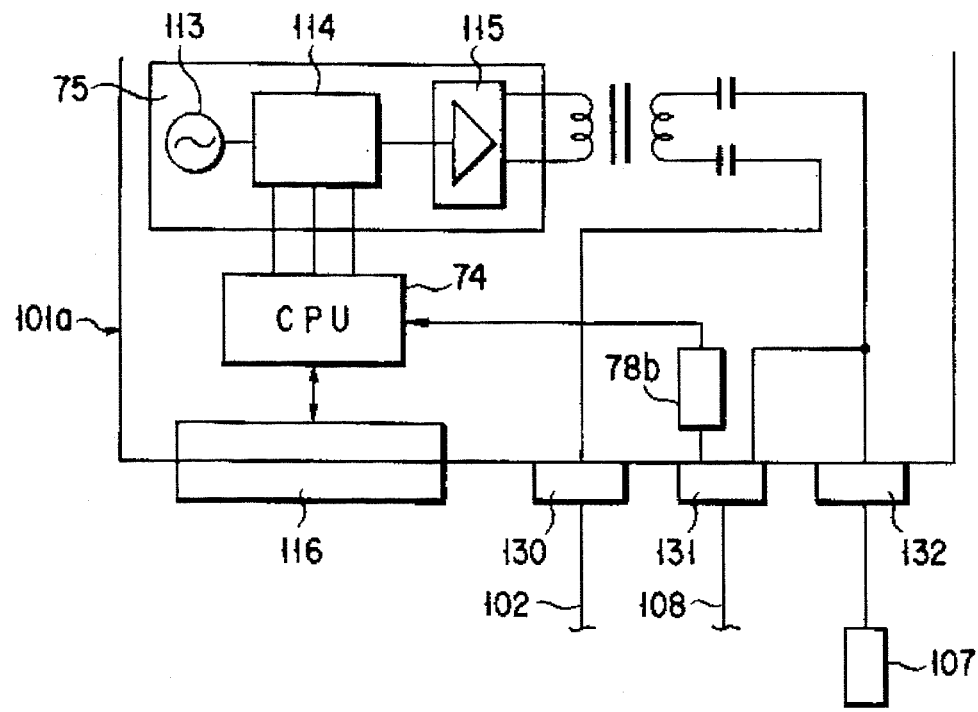
F I G. 18
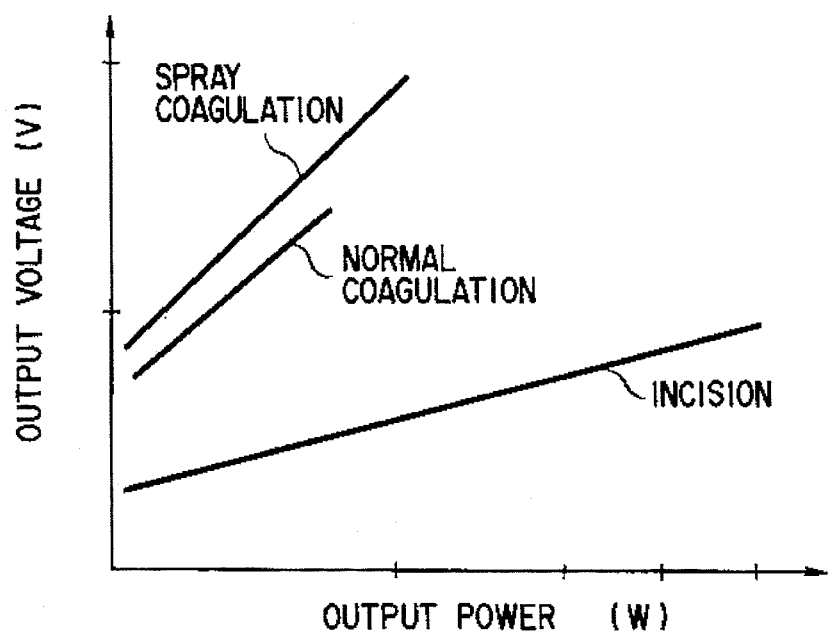
F I G. 19

HIGH FREQUENCY CAUTERIZING APPARATUS

BACKGROUND OF THE INVENTION

1. Field of the Invention

The present invention relates to a high-frequency (HF) cauterizing apparatus for medical treatment, with which incision of a living body tissue or hemostasis is performed by using a high-frequency current.

2. Description of the Related Art

In the field of surgical operations and medical treatment, an HF cauterizing apparatus has conventionally been used to perform incision or hemostasis by coagulation. In the HF cauterizing apparatus, a high-frequency (HF) medical treatment instrument is connected to a high-frequency (HF) power supply, and power or current applied from the HF medical treatment instrument to an affected part of a living body is controlled at an optimal level by a control device provided in the HF power supply. Thereby, desired medical treatment can be effected.

For example, U.S. Pat. No. 5,152,762, U.S. Pat. No. 5,108,398, U.S. Pat. No. 4,938,761 and U.S. Pat. No. 4,532,924 disclose means for controlling an output from a high-frequency power supply at an optimal level. Specifically, an output current from an active electrode connected to the HF power supply and a feedback current from a neutral electrode are sensed and compared, thereby indirectly detecting a leak current, detecting an impedance between an active-electrode-side output terminal and a neutral-electrode-side feedback terminal of the HF power supply, or sensing a temperature of heat applied to an affected tissue surface by providing a temperature sensor at an end portion of a bipolar electrode. On the basis of detected information, the value of a high-frequency output is controlled and optimal high-frequency outputs can be supplied to meet requirements of various surgical operations and medical treatment.

Suppose that an impedance between the output terminal of the HF power supply, on the one hand, and the electrode, living body, feedback current and feedback terminal of the HF power supply, on the other hand, is calculated by detecting an output current and output voltage within the HF power supply, and a high-frequency output is controlled so as to optimize a current density between a distal electrode portion of the treatment instrument and the affected part of the living body. In this case, however, there are various types of HF medical treatment instruments to be connected to the HF power supply, and the impedance of the HF medical treatment instruments in respect of high-frequency power or the area of the electrode portion in contact with the living body is not uniform. Consequently, variance occurs among detected output voltage values, output current values and impedance values, and the density of current applied to the affected part varies. As a result, optimal electric energy cannot be supplied. In other words, the density of current or power applied to the affected part cannot be controlled at a high-efficiency, optimal level. Thus, desired incision treatment or coagulation hemostasis treatment cannot be effected. In the case where the employed HF treatment instrument is changed or other affected part is treated consequently, even if the same operator performs the treatment with the same HF power supply, the state of incision or coagulation hemostasis will differ.

Besides, even if a temperature rise at the affected part is detected by a temperature sensor provided at a distal end portion of a bipolar electrode in order to control the coagulation state, noise may mix in a detection signal, depending on a noise level of high-frequency current output from the HF power supply itself. The noise degrades the detection precision. Consequently, it is difficult to control the high-frequency output at a desired level.

As has been described above, in most cases, when the HF cauterizing apparatus is used, the output power applied to the affected part and the output time are set by the operator by rule of thumb, for example, by viewing the affected part by the naked eye.

Under the circumstances, some means needs to be provided to exactly identify the types of many HF medical treatment instruments and feed a high-frequency output at optimal level to the treatment instruments. To provide such means is not easy in the case of the HF cauterizing apparatus with the above structure. In the above HF cauterizing apparatus, the treatment instrument is connected to the HF power supply, thereby constituting an electrically closed circuit comprising, e.g. a resistor, a capacitor, a coil, etc. which are separately provided on the treatment instrument side. By supplying weak high-frequency power to the closed circuit, a high-frequency resistance value of each treatment instrument is detected.

The reason why such weak high-frequency power is supplied in this case is that electric shock due to application of lower-frequency power is dangerous. In addition, if a resistance component is detected with low-frequency power, detection precision lowers. On the other hand, if DC current is supplied, noise of high-frequency power, etc. tends to occur. Thus, supply of DC current is technically undesirable. This being the case, weak high-frequency power is supplied. A detection value of the high-frequency resistance value is an analog value, which cannot be recognized by a control unit (including a CPU) which performs actual control. Accordingly, the control is switched by a control unit which does not include a CPU. Specifically, detected resistance values are compared by a comparison circuit, etc., and the output circuit is switched in accordance with the high/low level of the resistance values. However, in terms of precision, there is a limit to the technique of switching the control by detecting many treatment instruments by the comparison circuit. Forcible switching of the control in this case results in an abnormal increase in circuit scale and is practically difficult. In the case of the above HF cauterizing apparatus, at most a few types of medical treatment instruments can be identified.

On the other hand, when endoscopical medical treatment is performed by using a high-frequency cauterizing apparatus, a cord for equalizing the potential of a living body-side electrode of a high-frequency medical treatment instrument to the potential of an endoscope body is used. For example, this cord is a cord for feeding back a leak current from the endoscope body.

When HF medical treatment is performed by introducing a high-frequency treatment instrument such as an electric scalpel into the human body (or the patient) via an endoscope, a high-frequency current is let to flow from the instrument-side active electrode connected to a high-frequency cauterizing apparatus to the body-side counter electrode plate opposed to the active electrode. Thereby, an affected part located between the active electrode and counter electrode is incised or outflowing blood due to incision is coagulated and stopped. In this case, high-frequency current from the instrument-side active electrode leaks to a metallic portion of the endoscope body, and, as a result, the operator who touched the metallic portion may suffer a burn or a normal tissue may be cauterized. In order to avoid this from occurring, the leak current feedback cord, for example, is connected to a braid (a braid tube) provided over substantially the entire insertion portion of the endoscope, thereby equalizing the potential of the patient-side counter electrode to that of the endoscope body via the feedback cord. Thus, the high-frequency current leaking to the endoscope body (braid) is recovered and safety for the operator or patient is ensured.

A high-frequency cauterizing apparatus used in a surgical operation may have a spray coagulation function. According to the spray coagulation, a high voltage is generated and discharged to coagulate blood. The spray coagulation is very advantageous in that blood coagulation (hemostasis) is effected apart from the patient's bleeding part. Normally, blood is coagulated by thermal effect of high-frequency current by putting an electrode into contact with the bleeding part. In this case, however, blood may adhere to the electrode or when the electrode is removed after coagulation, the coagulated part adhered to the electrode may be separated from the body tissue and bleeding may occur once again. According to the spray coagulation, however, hemostasis can be effected apart form the bleeding part, and therefore the above drawbacks of the normal blood coagulation technique, wherein the electrode is put in contact with the bleeding part, can be avoided.

Needless to say, if endoscopical treatment can be performed by using the HF cauterizing apparatus having the spray coagulation function, convenience of the cauterizing apparatus will be enhanced. In other words, if the spray coagulation is effected and endoscopical HF medical treatment is performed with use of a single HF cauterizing apparatus, the cauterizing apparatus can be effectively used. However, if the HF cauterizing apparatus having the spray coagulation function is combined with the endoscope, the following problem will occur in an aspect of electrical safety.

In general, the HF cauterizing apparatus having the spray coagulation function has three modes: 1) an incision mode for incising a living body tissue by high-frequency current, 2) a spray coagulation mode for coagulating a bleeding part by electric discharge, and 3) a normal coagulation mode for coagulating blood with an electrode put in contact with a bleeding part. As is shown in FIG. 19, an output voltage (V) increases in proportion to an output power (W) in each mode. When the output power (W) is the same, the output voltages in the coagulation modes are higher than that in the incision mode, and the output voltage in the spray coagulation mode is higher than that in the normal coagulation mode. In general, electric discharge occurs more easily in the spray coagulation mode than in the normal coagulation, from the standpoint of waveforms.

Accordingly, if the spray coagulation function for coagulating blood of a bleeding part by generating high voltage and causing discharge is performed at the time of using the endoscope, there is a concern that an electric discharge occurs on the endoscope side. If the high-voltage discharge due to the spray coagulation acts on devices such as the endoscope, insulation breakage occurs in these devices and the operator may suffer a burn. In particular, the withstand voltage of endoscopes and HF treatment instruments for use in the field of internal treatment is lower than that of these devices for use in the field of surgical treatment. Besides, in general, it is not preferable, from the standpoint of withstand voltage, to use the spray coagulation function in the endoscopical treatment. Even if the aforementioned endoscope cord is used for the purpose of electrical safety, the problem due to high-voltage discharge of spray coagulation cannot be avoided.

More specifically, even if endoscopical treatment can be performed by using the HF cauterizing apparatus with the spray coagulation function, the aforementioned problem will occur if the spray coagulation function is erroneously performed. Thus, when the HF cauterizing apparatus with the spray coagulation function is combined with the endoscope in consideration of the aforementioned advantage, it is necessary to use the leak current feedback cord and ensure electrical safety.

SUMMARY OF THE INVENTION

The object of the present invention is to provide a high-frequency cauterizing apparatus which can perform optimal output control for any type of high-frequency medical treatment instrument, irrespective of the type of the high-frequency medical treatment instrument, has a spray coagulation function, and is capable of safely performing endoscopical high-frequency treatment.

This object can be achieved by a high-frequency cauterizing apparatus comprising: a high-frequency power supply device, having a plurality of high-frequency output modes, for generating a high-frequency current; at least one medical treatment instrument to be connected to the high-frequency power supply device; detection means for detecting connection of the medical treatment instrument to the high-frequency power supply device; control signal generating means for identifying the type of the medical treatment instrument on the basis of a detection signal from the detection means and generating a control signal; and control means for controlling a high-frequency output from the high-frequency power supply device on the basis of the control signal generated from the control signal generating means.

In particular, when the high-frequency cauterizing apparatus has a spray coagulation mode, the high-frequency cauterizing apparatus includes detection means for detecting connection of a leak current feedback cord electrically connected to the body of the endoscope to the nigh-frequency power supply device, and control means for controlling an output in at least a spray coagulation mode among the plurality of high-frequency output modes, on the basis of a detection signal from the detection means for detecting the connection of the leak current feedback cord.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 6 shows a drive circuit provided within a high-frequency power supply and various medical treatment instruments detachably connected to the drive circuit;

FIG. 7 illustrates an example of a signal transmission mode from a detection circuit to a control circuit provided in the drive circuit shown in FIG. 6;

FIG. 8 illustrates another example of the signal transmission mode from the detection circuit to control circuit provided in the drive circuit shown in FIG. 6;

FIG. 12 is a side view of the treatment instrument of the HF cauterizing apparatus according to the second embodiment of the invention;

FIG. 13 is an enlarged view of an electrode provided on a distal end portion of the treatment instrument shown in FIG. 12;

FIG. 14 is a cross-sectional view taken along line 14—14 in FIG. 13;

FIG. 15 shows schematically the entire structure of a high-frequency cauterizing apparatus according to a third embodiment of the present invention;

FIG. 16 is a front view of a front panel of a high-frequency power supply included in the HF cauterizing apparatus shown in FIG. 15;

FIG. 18 shows the structure of a main part of an internal circuit of the HF power supply; and FIG. 19 is a characteristic graph showing the relationship between an output voltage (V) and an output power (W) in a spray coagulation mode, a normal coagulation mode and an incision mode of the HF cauterizing apparatus.

DETAILED DESCRIPTION OF THE PREFERRED EMBODIMENTS

Figure 1:
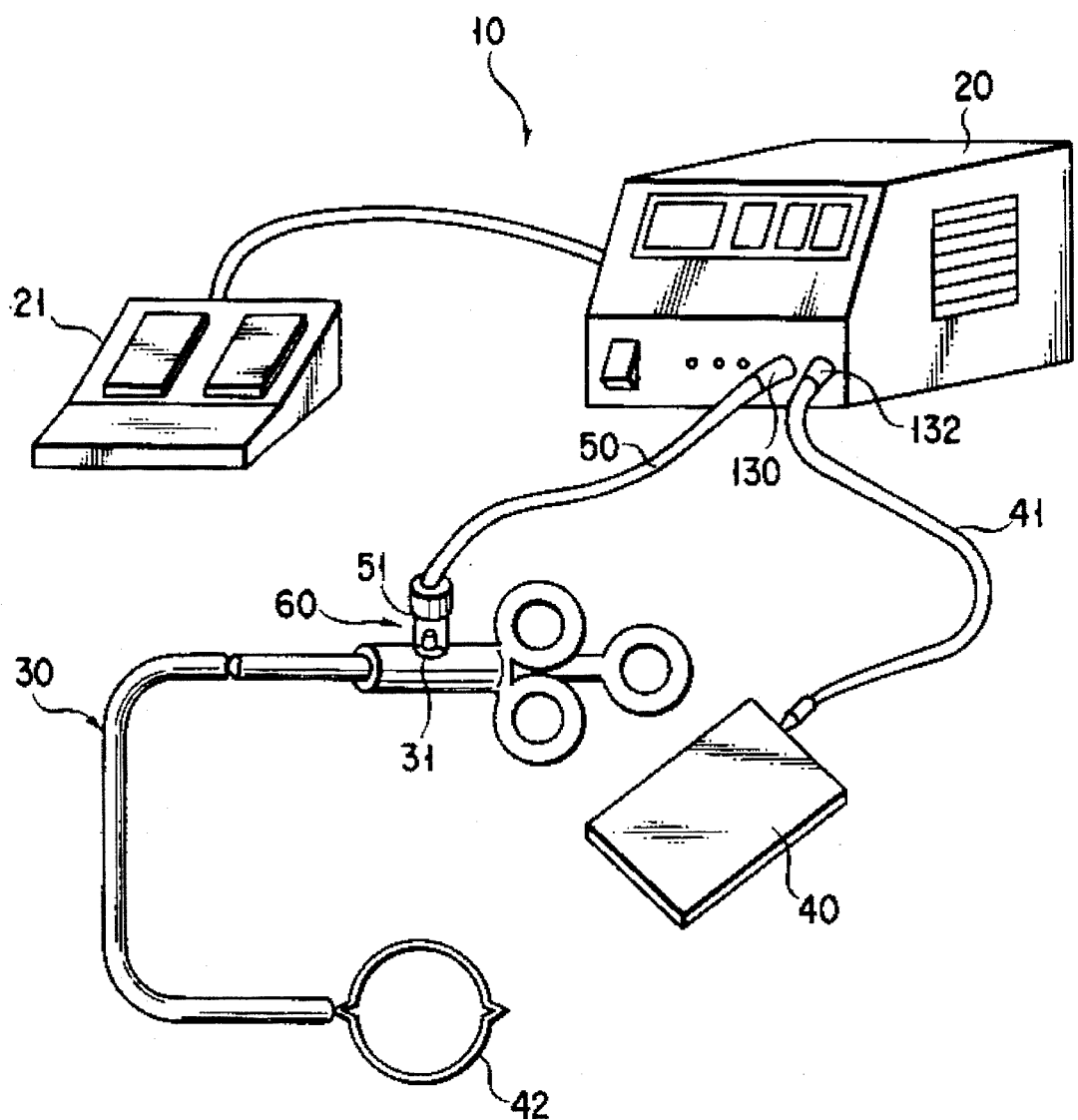
FIG. 1 is a perspective view showing schematically the entire structure of a high-frequency (HF) cauterizing apparatus according to a first embodiment of the present invention.

Embodiments of the present invention will now be described with reference to the accompanying drawings. FIGS. 1 to 8 shows a first embodiment of the present invention. FIG. 1 shows schematically the structure of a high-frequency (HF) cauterizing apparatus 10.

The HF cauterizing apparatus 10 comprises a high-frequency (HF) power supply 20, a high-frequency (HF) medical treatment instrument 30 with an instrument-side electrode (active electrode) 42 to be put in contact with a patient's affected part to be treated, and a patient-side electrode (counter electrode plate) 40 electrically connected to the HF power supply 20 via a connection cable 41. As is obvious from this structure, the treatment instrument 30 is of the mono-polar type, and it is combined with the counter electrode plate 40 to perform cauterizing treatment on the affected part. In this case, the HF power supply 20 includes output means matching with the mono-polar type instrument 30.

The HF medical treatment instrument 30 is connected to the HF power supply 20 via a connection cable 50. A connector 51 serving as detection means is provided at a distal end portion of the cable 50. By coupling the connector 51 to an identifying connector 31 serving as detection means of the treatment instrument 30, the treatment instrument 30 is connected to the cable 50. In this case, the connector 51 and identifying connector 31 constitute a connection unit 60. Supply/stop of power to the HF treatment instrument 30 is effected by a foot switch 21 connected to the HF power supply 20. Various instruments, as shown in FIG. 6, may be used as the HF medical treatment instrument 30 connected to the cable 50. For example, such instruments include a handpiece 30a, an oviduct ligation instrument 30b to be used, e.g. a hard endoscope, various excision forceps 30c using high-frequency current, a high-frequency snare 30d which can be used with a soft endoscope 104, etc.

Figure 2:
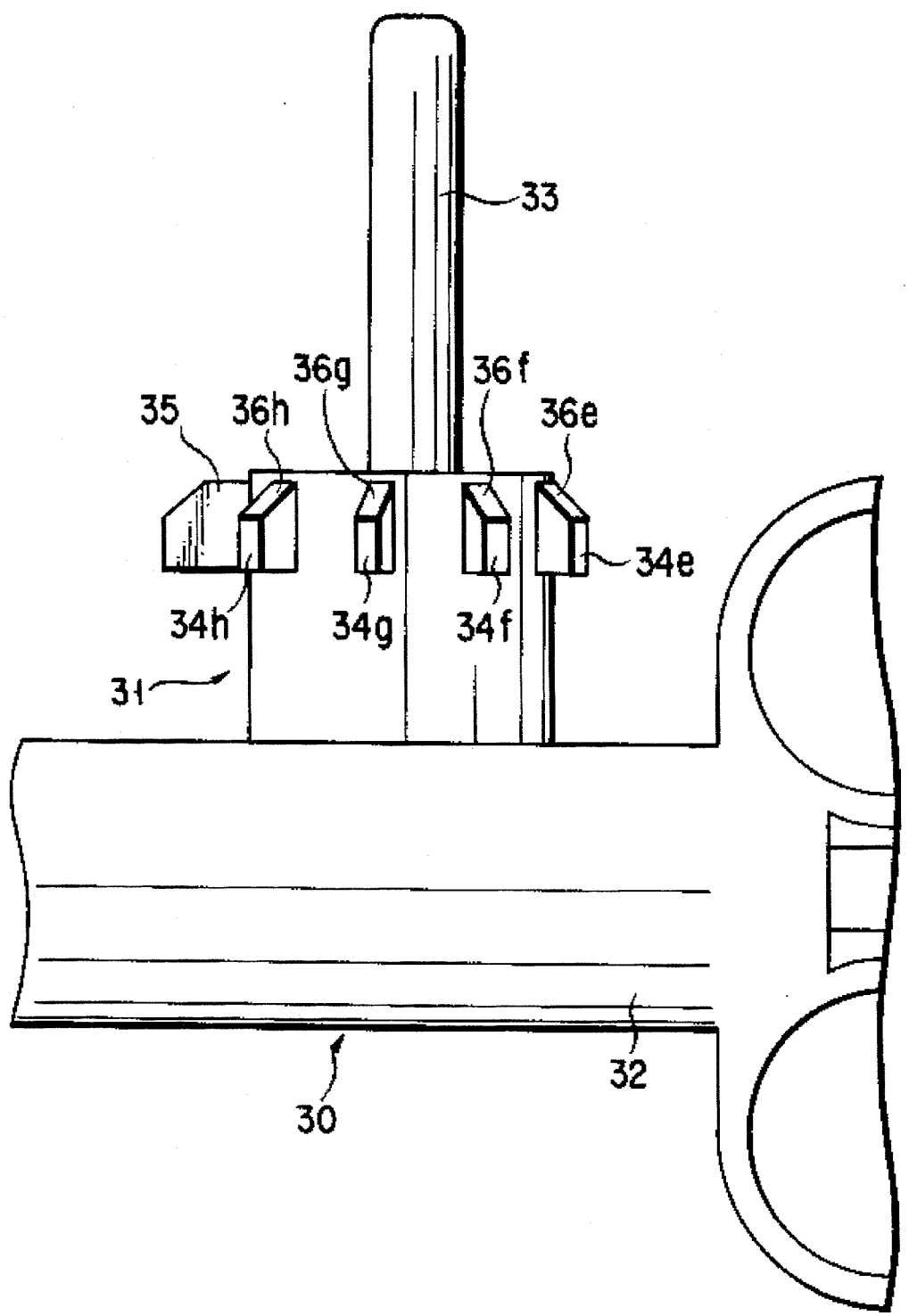
FIG. 2 shows, on an enlarged scale, an identifying connector provided on a medical treatment instrument included in the HF cauterizing apparatus shown in FIG. 1.
Figure 3:
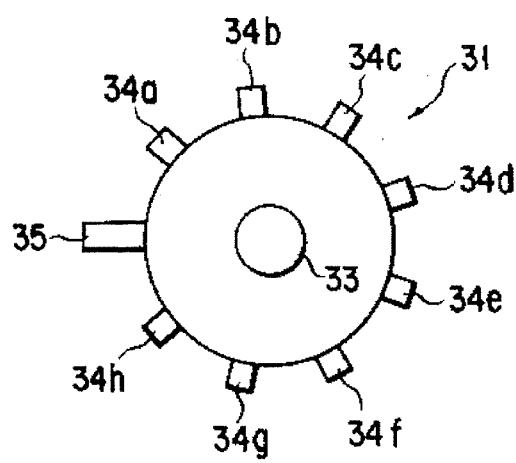
FIG. 3 is a plan view of the identifying connector shown in FIG. 2.

FIGS. 2 to 5 shows the connection unit 60 in detail. At first, the identifying connector 31 of the connection unit 60 will now be described with reference to FIGS. 2 and 3. As is shown in FIG. 2, the identifying connector 31 is provided at a proximal end-side large-diameter portion 32 of the HF medical treatment instrument 30. The identifying connector 31 includes a high-frequency (HF) connection pin 33 provided at a substantially central portion thereof, a plurality of identification keys (ID keys) 34 provided on the outer peripheral surface of the connector 31 for indicating high-frequency characteristics of the HF treatment instrument 30, and an erroneous insertion prevention key 35 formed to have a greater size than each ID key 34. The ID keys 34 are arranged on the outer peripheral surface of the connector 31 at regular intervals. For example, if eight ID keys 34 can be arranged on the outer peripheral surface of the identifying connector 31, 256 types of HF treatment instrument 30 can be identified according to their high-frequency characteristics, on the basis of the arrangement state and the number of the ID keys 34. Specifically, if the state in which none of ID keys 34 is provided is represented by hexadecimal "0" and the state in which all eight ID keys 34a, 34b, . . . , 34h are provided is represented by "FF", the number of combinations of the eight ID keys 34a to 34h is 256. Thus, 256 types of HF medical treatment instruments 30 can be identified.

Figure 4:
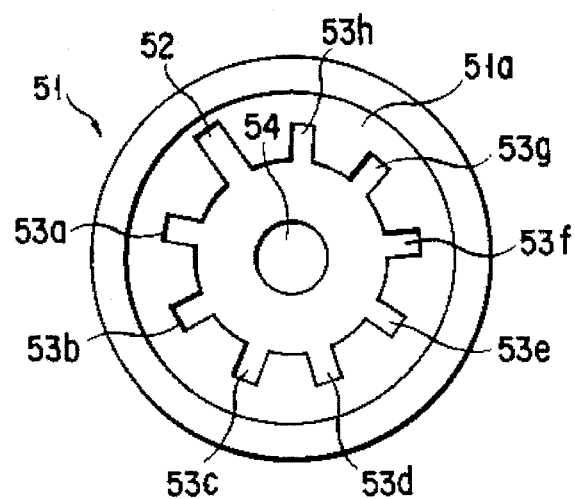
FIG. 4 is a plan view showing a connector provided on a high-frequency (HF) power supply section included in the HF cauterizing apparatus shown in FIG. 1.

Now referring to FIGS. 4 and 5, the connection 51 to be connected to the identifying connector 31 will be described. A distal end portion 51a of the connector 51 coupled to the connection cable 50 is provided with a key groove 52 for insertion of the erroneous insertion prevention key 35 of identifying connector 31, and ID key grooves 53a to 53h for insertion of the ID keys 34a to 34h of the identifying connector 31. An inner portion of the connector 51 is provided with a high-frequency (HF) electrode portion 54 to be connected to the HF connection pin 33 of the identifying connector 31.

Figure 5:
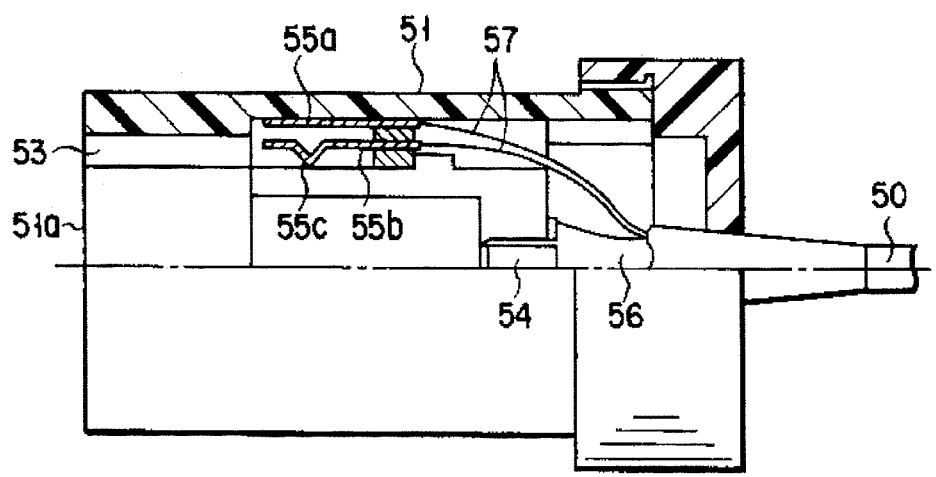
FIG. 5 is a cross-sectional side view of the connector shown in FIG. 4.

FIG. 5 shows an internal structure of each ID key groove 53. A pair of contact points 55a and 55b serving as detection means are provided in an inner part of each ID key groove 53. The first contact point 55a is situated radially outward, and the second contact point 55b is situated radially inward and has a bent portion 55c. The HF electrode portion 54 is coupled to an HF output cable 56 connected to the HF power supply 20. The HF output cable 56 and signal lines 57 connected to the contact points 55a and 55b are passed through the connection cable 50 and electrically connected to a detection circuit 78a (see FIGS. 6 to 8) provided within the HF power supply 20.

When the connector 51 is coupled to the identifying connector 31, the erroneous insertion prevention key 35 formed on the identifying connector 31 is situated at the key groove 52 formed in the connector 51. In this state, the ID key 34 is inserted in the associated ID key groove 53. Thus, a beveled portion 36 (see FIG. 2) formed on the ID key 34 is put in contact with the bent portion 55c of the second contact point 55b. The ID key 34 is further inserted in the ID key groove 53, and the second contact point 55b is raised radially outward and brought into contact with the first contact point 55a. As a result, the signal cables 57 connected to the contact points 55a and 55b constitute a closed circuit, and a detection signal representing this closed-circuit state is transmitted to the detection circuit 78a (see FIG. 6) provided within the HF power supply 20. In this manner, in the ID key groove 53 in which the ID key 34 has been inserted, the contact points 55a and 55b are connected to constitute the closed circuit and the detection signal representing the closed-circuit state is transmitted to the detection circuit 78a of the HF power supply 20. On the other hand, in the ID key groove 53 in which the associated ID key 34 has not been inserted, the contact points 55a and 55b are not connected and the circuit including the contact points 55a and 55b is left open and no detection signal is generated. Accordingly, the detection circuit 78a provided within the HF power supply 20 detects the presence/absence of the detection signal to be generated in accordance with the closed/open state of the circuit of the contact points 55a and 55b. In other words, the detection circuit 78a detects the ID key groove 53 from which the detection signal has been generated and the ID key groove from which no detection signal has been generated, thereby to identify the type of the HF treatment instrument 30 connected to the connector 51.

With reference to FIGS. 6 to 8, a drive circuit 82 having the detection circuit 78a for identifying the type of the type of the HF treatment instrument 30 and a control circuit 74 for controlling a high-frequency (HF) oscillation output on the basis of a signal from the detection circuit 78a.

As is shown in FIG. 6, the drive circuit 82 comprises mainly the detection circuit 78a for identifying the type of the HF treatment instrument 30 by detecting the detection signal from the signal cable 57; a converter circuit 72 for converting an identification signal (ID signal) from the detection circuit 78a to a predetermined mode signal (control signal) capable of activating the drive circuit 82; the control circuit 74 for generating a drive signal based on the signal from the converter circuit 72 and delivering it to a high-frequency (HF) oscillation unit 75; and the HF oscillation unit 75 for oscillating an HF output based on the drive signal from the control circuit 74. The HF oscillation unit 75 comprises a waveform generator 75a for generating an HF current waveform suitable for incision or coagulation on the basis of the drive signal from the control circuit 74; a power amplifier 75b for amplifying a magnitude (power) of the waveform generated by the waveform generator 75a; and a switching circuit 75c for selectively delivering the HF output to a mono-polar section or a bipolar section. A memory provided in the control circuit 74 stores, in advance, optimal output conditions of the various HF treatment instruments 30. Thus, if the type of the connected treatment instrument 30 is identified by the detection circuit 78a, the resultant ID signal is converted to a control signal by the converter circuit 72. Based on the control signal, the control circuit 74 reads out the optimal output condition of the associated treatment instrument from the memory and controls the HF oscillation unit 75 so that the HF output may meet the optimal output condition.

The drive circuit 82 is applicable to not only the mono-polar type treatment instrument 30, as is employed in the present embodiment, but also to a bipolar type treatment instrument 90, as in a second embodiment of the invention, and to a treatment instrument in which an endoscope and the mono-polar type instrument 30 are combined, as in a third embodiment of the invention. Accordingly, the HF power supply 20 includes an active connector 130 for connection with the cable 50 coupled to the treatment instrument-side electrode 42 of the mono-polar type instrument 30 (30a to 30d); a patient connector 130 for connection with the cable 41 coupled to the patient-side electrode 40; a connector 62, as is used in the second and third embodiments; and an S-cord connector 131 fox connection with an S-cord 108 (described later) coupled to the endoscope 104. In addition, the HF power supply 20 includes a detection circuit 78c (described later) for identifying the type of the bipolar type instrument 90 coupled to the connector 62, a converter circuit 73 for converting an ID signal from the detection circuit 78c to a predetermined mode signal, and a detection circuit 78b for detecting the connection between the S-cord 108 of the endoscope 104 and the S-cord connector 131. The S-cord 108 coupled to the S-cord connector 131 is electrically connected to the counter electrode plate 40 by the internal circuit of the HF power supply 20 and is kept at the same potential as the counter electrode plate 40. The structures and functions of the connectors 62, 131 and 132, the detection circuit 78c and the converter circuit 73 will be described in detail in the second and third embodiments.

FIGS. 7 and 8 show examples of a signal transmission mode from the detection circuit 78a (78c) to the control circuit 74 via the converter circuit 72 (73). In the present embodiment, the type of the instrument 30 to be recognized based on mechanical connection of the connectors 31 and 51 is detected by the detection circuit 78a (78c). Since the output signal from the detection circuit 78a (78c) is an analog signal, the converter circuit 72 (73) needs to function as an A/D converter circuit for converting an analog signal to a digital signal. In this case, based on the digital signal from the converter circuit (A/D converter circuit) 72 (73), the control circuit (CPU) 74 outputs a drive signal to the HF oscillation unit 75. In this structure, the detection signal from the detection circuit 78a (78c) is converted by the converter circuit 72 (73) to a signal (control signal) which can easily be recognized by the CPU 74. Thereby, many instruments 30 can be identified with simple construction.

On the other hand, if the output signal from the detection circuit 78a (78c) is a digital signal, the converter circuit 72 (73) functions as a decoding circuit for analyzing the digital signal. Since the output signal from the detection circuit 78a (78c) is already a digital signal, the digital signal is decoded by the converter circuit 72 (73) and supplied as a selector signal to the control circuit 74 (constituted not by a CPU). As is shown in FIG. 8, a plurality of control circuits 74 may be provided. On the basis of the output signal from the detection circuit 78a (78c), the decoding circuit 72 (73) produces a select signal and a predetermined one of the control circuits 74 is activated by the select signal. This construction is easily applied to the control circuit having no CPU.

As has been described above, when the connector 51 is coupled to the identifying connector 31, the contact points in the ID key grooves 53 of the connector 51 are turned on/off so that the type of the HF treatment instrument 30 is identified. On the basis of the ID information, the HF output is controlled to agree with the value pre-stored in the memory in the control circuit 74 of the HF power supply 20 as an optimal output condition of each HF treatment instrument. When an affected part (e.g. polyp) of a living body tissue is incised with the HF treatment instrument under the optimal output condition, the patient-side electrode 40 is attached to the living body tissue by means of an adhesive, etc. Then, the ring-shaped instrument-side electrode 42 is hooked on the polyp and the polyp is ligated. In this state, a high-frequency current is supplied to the instrument-side electrode 42 from the HF cauterizing apparatus 10. The HF current flows from the instrument-side electrode 42 to the patient-side electrode 40 via the living body tissue including the polyp. Thus, the polyp is incised.

As has been described above, according to the HF cauterizing apparatus 10 of the present embodiment, the difference in living-body contact area and high-frequency resistance value among treatment instruments are exactly detected on the basis of mechanical connection between the connectors 31 and 51. Thus, output current/voltage of the HF cauterizing apparatus is controlled so that an optimal current density is obtained between the instrument-side electrode 42 and the affected part. Thereby, incision or hemostasis by coagulation can be performed with efficient, optimal electric energy. In other words, irrespective of the types of the HF treatment instruments 30, optimal output control can be effected for the respective HF treatment instruments 30. Accordingly, the precision in control of the high-frequency current/voltage for different instruments 30 is enhanced, and uniform medical treatment can be performed irrespective of differences in surgical operational environment, affected parts, and surgical operators.

The HF cauterizing apparatus 10 of the present embodiment has a practically excellent advantage in that the types of many treatment instruments 30 can be identified without providing an electric device such as impedance element on the section of the instrument 30. Needless to say, however, this advantage can be obtained when such an electric device is provided.

FIGS. 9 to 14 show a second embodiment of the invention. The high-frequency treatment instrument 90 of the HF cauterizing apparatus according to the second embodiment is of the bipolar type. A distal end portion of the instrument 90 is provided with a hook-shaped bipolar electrode 91 (see FIG. 14). The bipolar electrode 91, excluding a distal end portion thereof, is covered with an insulating tube 92. That part of the electrode 91, which is covered with the insulating tube 92, is substantially provided in an insertion tube 93. A connection cable 50 is extended from a side portion of a large-diameter portion 94 provided at a proximal end side of the insertion tube 93. A connection port 95 to be connected to a water supply tube is provided at a proximal end portion of the large-diameter portion 94. The bipolar electrode 91 will be described later.

Figure 9:
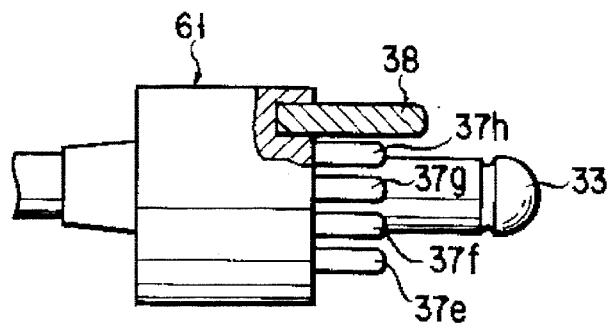
FIG. 9 shows, on an enlarged scale, an identifying connector provided on a medical treatment instrument of a high-frequency cauterizing apparatus according to a second embodiment of the invention.
Figure 10:
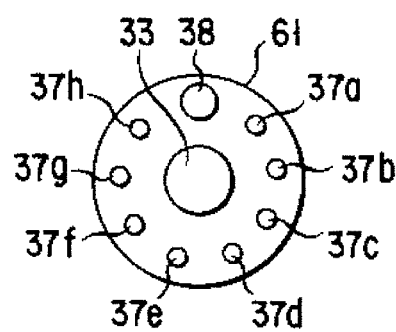
FIG. 10 is a plan view of the identifying connector shown in FIG. 9.

As is shown in FIG. 12, an identifying connector 61, which constitutes a part of the connection unit 60 of this embodiment, is provided at a distal end portion of the connection cable 50 extending from the HF treatment instrument 90. As is shown in FIGS. 9 and 10, the identifying connector 61 has an HF connection pin 33 at a substantially central portion of the insulating connector body. Eight identification pins (ID pins) 37a to 37h and an erroneous insertion prevention pin 38, which is longer and thicker than each ID pin 37, are provided substantially concentrically around the HF connection pin 33.

Figure 11:
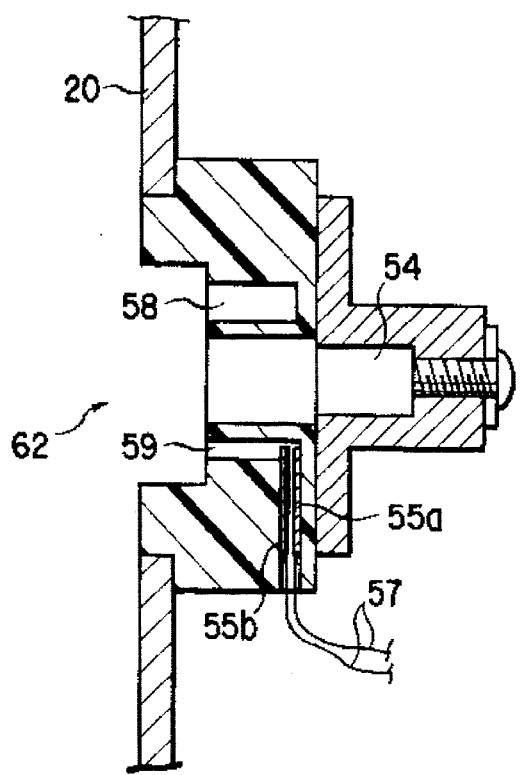
FIG. 11 is a cross-sectional side view showing a connector provided on a high-frequency power supply section of the HF cauterizing apparatus.

On the other hand, a connector 62 to be coupled to the identifying connector 61 is provided on the HF power supply 20, as shown in FIG. 11. The connector 62 has an insertion hole 58 for insertion of the erroneous insertion prevention pin 38 of the identifying connector 61 and insertion holes 59a to 59h for insertion of the ID pins 37a to 37h of the identifying connector 61. A high-frequency (HF) electrode 54, in which the HF connection pin 33 is to be fitted, is provided at an inner portion of the connector 62. A pair of contact points 55a and 55b are provided in an inner part of each insertion hole 59. In this case, the first contact point 55a is situated more inward than the second contact point 55b. The other structural features of the second embodiment are the same as those of the first embodiment.

In the above construction, when the identifying connector 61 is coupled to the connector 62, the ID pin 37 is inserted in the associated insertion hole 59, thus pushing the second contact point 55b into contact with the first contact point 55a. An ID signal representing this connection state is transmitted to the detection circuit 78c (see FIG. 6) of the HF power supply 20. The detection circuit 78c has identified the type of the instrument 90 and feeds an output signal to the control circuit 74 via the converter circuit 73. The other operations of the second embodiment are the same as those of the first embodiment.

In the second embodiment, there is no need to pass signal lines 57 extending from the first and second contact points 55a and 55b through the connection cable 50. Thus, the structure of the connection unit 60 can be simplified.

The electrode 91 of the HF treatment instrument 90 will now be described. As has been described above, according to the structures of the first and second embodiments, the characteristics such as HF resistance of the HF treatment instrument 30 (90) are exactly identified by the identifying means constituted by the connector 51 (62) and identifying connector 31 (61). Thereby, optimal waveform outputs for incision and coagulation hemostasis operations, which are principal outputs of the HF treatment instrument 30 (90), can be supplied. However, in order to efficiently apply the optimal waveform output to the affected part of the patient for incision or coagulation hemostasis operations, the following conditions must be satisfied. In the case of incision, it is necessary to reduce to a minimum the contact area between the electrode of the HF treatment instrument and the affected part, thereby to increase the density of current applied to the body tissue of the affected part. In the case of hemostasis by coagulation, it is necessary to increase as much as possible the contact area between the electrode of the HF treatment instrument and the affected part, thereby to decrease the density of current applied to the body tissue of the affected part. Moreover, if insulation of an electrode is effected by air, the size of the electrode is increased and the electrode has a simple circular shape. In this case, the electrode is suitable for hemostasis by coagulation but not for incision.

To solve these problems, the electrode 91 of the HF treatment instrument of the second embodiment has the following structure.

As is shown in FIG. 14, the electrode 91 has a hook shape and is electrically separated into two parts by an insulating member 96. The electrode has such a substantially trapezoidal cross section that a side face 97 for coagulation hemostasis is large and a side face 98 for incision is small.

According to the above structure, since the bipolar electrode 91 is formed with use of the insulating member 96, the size thereof is substantially the same as that of a mono-polar electrode. In addition, since the side face 97 for coagulation hemostasis is large, the contact area between the electrode 91 and the affected part increases and the density of current applied to the affected part can be decreased. Besides, since the side face 98 for incision is small, the contact area between the electrode 91 and the affected part decreases and the density of current applied to the affected part can be increased. Accordingly, proper coagulation hemostasis or incision can be performed with optimal output.

The electrode 91 of the HF treatment instrument 90 may be of a straight type or a right-angle type.

FIGS. 15 to 18 show a third embodiment of the invention. An HF power supply 101a of an HF cauterizing apparatus of the third embodiment is provided with two output means, i.e. bipolar output means and mono-polar output means. A bipolar selection switch 118 and a mono-polar selection switch 119 for selecting the output means are provided on a front panel (see FIG. 16).

The HF power supply 101a has an incision mode for incising a body tissue by high-frequency current, a spray coagulation mode for coagulating a bleeding part by electric discharge, and a normal coagulation mode for coagulating blood with an electrode put contact with a bleeding part. One of these modes can be selected. Specifically, the HF power supply 101a enables either incision treatment or coagulation treatment to be effected in accordance with an oscillation mode thereof. With respect to the coagulation treatment, a coagulation mode selection switch 123 and a spray coagulation mode selection switch 124 for respectively selecting the normal coagulation mode and spray coagulation mode are provided on the front panel. With respect to the incision treatment (or "cutting treatment"), a pure incision mode for generating a continuous wave and blend modes 1 and 2 for varying the rate of occurrence of continuous waves in the incision mode are provided. an incision mode switch 120, a blend mode 1 switch 121 and a blend mode 2 switch 122 for respectively selecting these modes are provided on the front panel. Light emitting diodes (LED) for indicating the presently selected output means and mode are provided near the selection switches.

The front panel has a first connection unit 135 and a second connection unit 136 to which HF treatment instruments are connected. The first connection unit 135 is connected to a bipolar HF treatment instrument such as a surgical electric scalpel. The second connection unit 136 is connected to a mono-polar HF treatment instrument (e.g. a high-frequency snare 103 (see FIG. 15) having a ring-shaped wire treatment portion 103a which is hooked on a polyp 140 of a body tissue 106 and iigates and incises the polyp 140) and a counter electrode plate 107 used in combination with the HF snare 103. Accordingly, the second connection unit 136 is provided with an active connector 130 for connection with an active electrode 102 having the treatment portion 103a at a distal end thereof, and a patient connector 132 for connection with a counter electrode plate 107 to be attached to the body tissue 106 in combination with the active electrode 102. The second connection unit 136 is also provided with an S-cord connector 131 for connection with a leak current feedback cord ("S-cord") for equalizing the potential of the endoscope 104 to that of the counter electrode plate 107. The S-cord 108 is connected to, e.g. a braid (a braid tube) provided over substantially the entire length of an insertion portion of the endoscope 104. As will be described later, the potential of the patient-side counter electrode plate 107 is equalized to that of the body of the endoscope 104 via the HF power supply 101a, whereby high-frequency current leaking to the body (braid) of the endoscope 104 is recovered and the safety for the operator or patient is ensured. The HF power supply 101a is connected to a foot switch 109 for turning on/off a high-frequency output.

When the polyp 140 of body tissue 106 is incised by the HF snare 103, the insertion portion of the HF snare 103 is introduced into the human body through a channel of the endoscope 104. Then, an operation handle 105 of the snare 103 is actuated to activate the ring-shaped treatment portion 103a connected to the active electrode 102. Thus, the treatment portion 103a is hooked on, and ligates, the polyp 140. On the other hand, the counter electrode plate 107 is attached to the body tissue 106 by an adhesive, etc. If high-frequency current is let to flow from the HF power supply 101a to the active electrode 102, the HF current flows from the active electrode 102 to the counter electrode plate 107 via the body tissue 106 including polyp 140 and the polyp 140 is incised.

The circuit for controlling the high-frequency output will now be described with reference to FIG. 18.

The potential of the body of the endoscope 104 is equalized to that of the counter electrode plate 107 via the S-cord 108 connected to the body of endoscope 104. Specifically, the other end of the S-cord connected to the S-cord connector 131 is electrically connected to the counter electrode plate 107 within the circuit of the HF power supply 101a, as shown in FIG. 18. Thus, the potential of the body of the endoscope 104 is equalized to that of the counter electrode plate 107.

The circuit shown in FIG. 18 includes the detection circuit 78b for detecting the connection between the S-cord 108 and the S-cord connector 131. The detection circuit 78b is electrically connected to the CPU 74. The CPU 74 is electrically connected to the HF oscillation unit 75 and a display panel 116. As is shown in FIG. 6, the converter circuit 72 may be provided between the detection circuit 78b and the CPU 74, and the active connector 130 may be connected to the CPU 74 via the detection circuit 78a and converter circuit 72. In this case, like the first embodiment, the HF output is controlled in accordance with the type of the treatment instrument connected to the active connector 130.

The HF oscillation unit 75 comprises an oscillator 113, a modulator 114 and an amplifier 115. In the oscillation unit 75, a signal output from the oscillator 113 is modulated by the modulator 114 to generate a waveform suitable for incision or coagulation, and the waveform is amplified by the amplifier 115. The modulator 114 can also modulate the magnitude (power) of the waveform. The shape and magnitude of the waveform generated by the modulator 114 are controlled by a control signal output from the CPU 74.

The circuit configuration of the HF power supply 101a is substantially the same as that of the HF power supply 20, except for the parts shown in FIG. 18.

Figure 17:
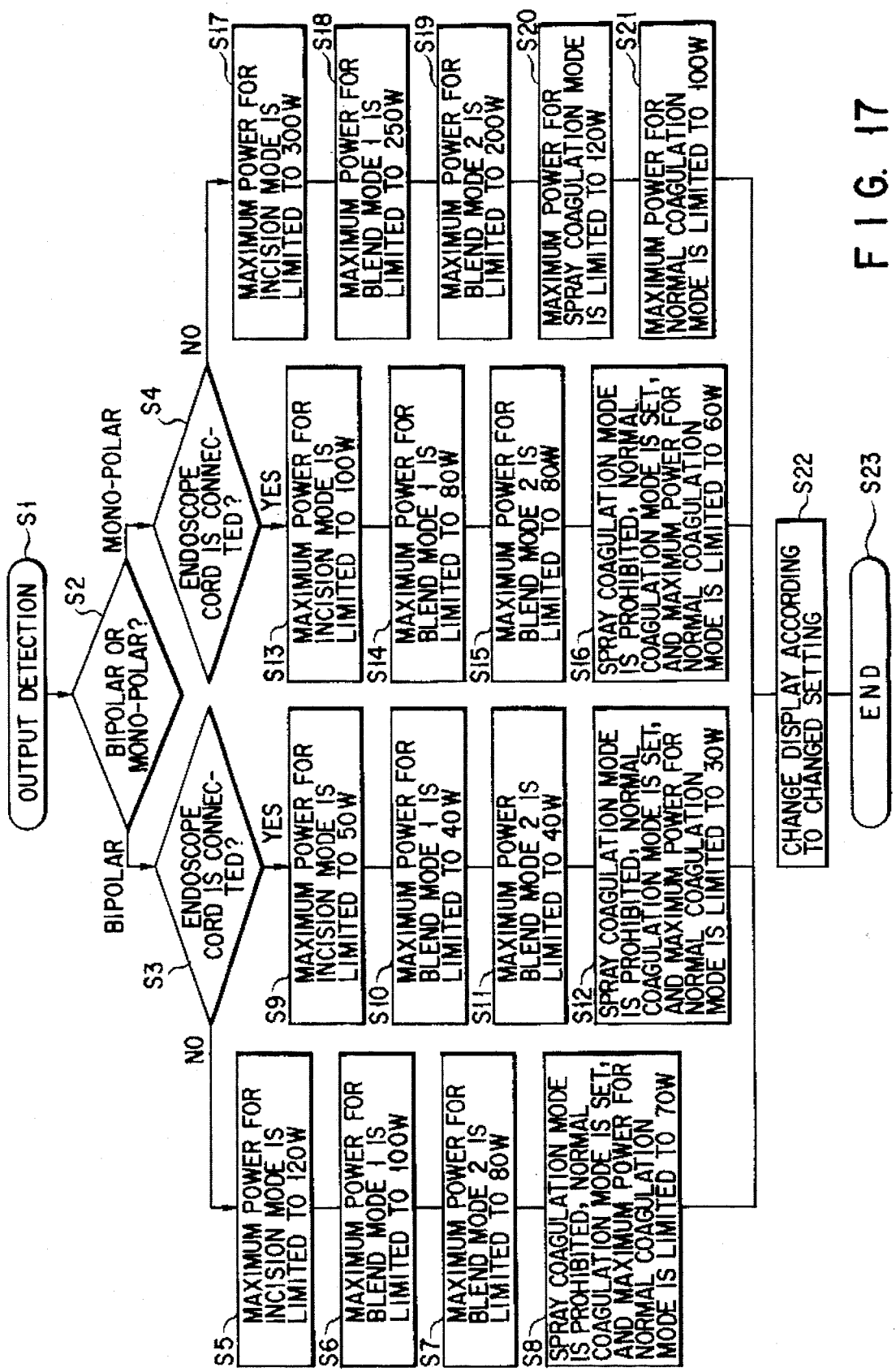
FIG. 17 is a flow chart illustrating the operation of the HF power supply shown in FIG. 16.

The operation of the HF power supply 101a of the third embodiment will now be described with reference to the flow chart of FIG. 17.

Either the bipolar selection switch 118 or mono-polar selection switch 119 is turned on to set the bipolar output mode or mono-polar output mode. The output mode signal is recognized by the CPU 74 (steps S1 and S2).

The operation in the case where the mono-polar output mode is selected will be described. In the mono-polar output mode, the spray coagulation operation can be performed. The S-cord connection detecting circuit 78b detects connection/disconnection of the S-cord 108 (step S4). If the S-cord 108 is not 10 connected, the maximum power for each of the incision and coagulation modes is set at a normal maximum value. Specifically, the maximum power for the incision mode is limited to 300 W, the maximum power for the blend mode 1 is limited to 250 W, the maximum power for the blend mode 2 is limited to 200 W, the maximum power for the spray coagulation mode is limited to 120 W, and the maximum power for the normal coagulation mode is limited to 100 W (steps S17 to S21).

If the S-cord 108 is connected, the CPU 74 determines, via the S-cord connection detecting circuit 78b, that the endoscope 104 is being used, and controls the maximum power of each of the incision and coagulation modes. When the endoscope is used, the maximum powers are set at lower levels than the above-mentioned normal maximum values. In addition, when the endoscope is used, the output for the spray coagulation mode is stopped. Specifically, the maximum power for the incision mode is limited to 100 W, the maximum power for the blend mode 1 is limited to 80 W, the maximum power for the blend mode 2 is limited to 80 W, the maximum power for the normal coagulation mode is limited to 60 W, and the output for the spray coagulation mode is stopped (steps S13 to S16).

The operation in the case where the bipolar output mode is selected will now be described. When the S-cord 108 is not connected, the maximum power for each of the incision and coagulation modes is set at a normal maximum value. Specifically, the maximum power for the incision mode is limited to 120 W, the maximum power for the blend mode 1 is limited to 100 W, the maximum power for the blend mode 2 is limited to 80 W, the maximum power for the normal coagulation mode is limited to 70 W, and the output for the spray coagulation mode is stopped (steps S5 to S8). When the S-cord 108 is connected, the CPU 74 determines, via the S-cord connection detecting circuit 78b, that the endoscope 104 is being used, and controls the maximum power of each of the incision and coagulation modes. When the endoscope is used, the maximum powers are set at lower levels than the above-mentioned normal maximum values in steps S5 to S8. In addition, when the endoscope is used, the output for the spray coagulation mode is stopped. Specifically, the maximum power for the incision mode is limited to 50 W, the maximum power for the blend mode 1 is limited to 40 W, the maximum power for the blend mode 2 is limited to 40 W, the maximum power for the normal coagulation mode is limited to 30 W, and the output for the spray coagulation mode is stopped (steps S9 to S12).

In the present embodiment, when the S-cord 108 is connected to the HF power supply 101a, the S-cord connection detecting circuit 78b detects the connection and supplies the detection signal to the CPU 74. If the currently selected mode is the spray coagulation diode, the CPU 74 forcibly changes the mode to the normal coagulation mode and prohibits the spray coagulation mode. As to the modes other than the spray coagulation mode, the maximum value of the HF output is changed to the preset maximum value for endoscopical treatment (which is lower than the value at the time the S-cord 108 is not connected). The maximum power values are not limited to those indicated in FIG. 17 and may be changed according to conditions.

As has been described above, according to the HF power supply 101a of the present embodiment, at the time of the endoscopical medical treatment, the output in the spray coagulation mode is prohibited and the maximum value of HF output in each of the other modes is made lower than the normal value. Thereby, dielectric breakdown of the endoscope 104 and HF treatment instrument 105 with relatively low withstand voltages can be prevented, and high-frequency current is prevented from flowing to the operator. In particular, the withstand voltage of a high-frequency snare or an endoscope used in internal treatment is lower than that of a surgical electric scalpel. In using the snare or endoscope, the HF power supply 101a can be used safely. In other words, with the HF power supply 101a of this embodiment, although the spray coagulation operations can be performed, the spray coagulation function is stopped or prevented when the endoscope is used. Thereby, the danger due to spray coagulation is limited to a minimum, dielectric breakdown of the endoscope or treatment instrument is prevented, and the danger of a burn on the operator is prevented with use of the S-cord 108.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A high-frequency cauterizing apparatus comprising:
   a high-frequency power supply device, having a plurality of high-frequency output modes, for generating a high-frequency current;
   at least one medical treatment instrument to be connected to said high-frequency power supply device;
   said at least one medical treatment instrument to be connected to said high-frequency power supply device comprising an endoscope and a high-frequency medical treatment instrument carried by said endoscope, said high-frequency medical treatment instrument having two electrodes, said two electrodes of said high-frequency medical treatment instrument including:
   a living body-side electrode for performing a cauterizing treatment for a living body tissue by a high-frequency current produced by said high-frequency power supply device, said living body-side electrode being arranged to be put in contacts with the living body, and
   a medical instrument-side electrode arranged to be put in contact with an affected part of a living body;
   detection means for detecting connection of said medical treatment instrument to said high-frequency power supply device;
   control signal generating means for identifying the type of the medical treatment instrument responsive to a detection signal from said detection means, and for generating a control signal; and
   control means for controlling a high-frequency output from said high-frequency power supply device on the basis of said control signal generated from said control signal generating means;
   said endoscope including a leak current feedback cord electrically connected to a body portion of said endoscope; and
   said high-frequency power supply device including means for equalizing a potential of the living body-side electrode of said high-frequency medical treatment instrument to that of the body portion of said endoscope via said leak current feedback cord.

2. The apparatus according to claim 1, wherein said detection means is provided at a connection unit between said high-frequency power supply device and said high-frequency medical treatment instrument.

3. The apparatus according to claim 2, wherein said detection means comprises:

an identifying connector provided on said high-frequency medical treatment instrument and having an identification key representing predetermined high-frequency characteristics of the high-frequency medical treatment instrument;

an electrode connector provided at an end portion of a connection cable connected electrically to said high-frequency power supply device and having an identification key groove in which said identification key of said identifying connector is to be inserted; and a detection unit for detecting said predetermined high-frequency characteristics of said high-frequency medical treatment instrument by electrically detecting a connection state between said identifying connector and said electrode connector.

4. The apparatus according to claim 3, wherein said detection unit includes two electrical contact points which are provided within said identification key groove and which are electrically connected to each other by said identification key of said identifying connector when said identification key is inserted into the identification key groove.

5. The apparatus according to claim 2, wherein said detection means comprises:

an identifying connector provided on an end portion of a connection member mechanically connected to said high-frequency medical treatment instrument and having an identification pin representing predetermined high-frequency characteristics of the high-frequency medical treatment instrument;

an electrode connector connected electrically to said high-frequency power supply device and having an identification hole in which said identifying pin of said identifying connector is to be inserted; and a detection unit for detecting said predetermined high-frequency characteristics of said high-frequency medical treatment instrument by electrically detecting a connection state between said identifying connector and said electrode connector.

6. The apparatus according to claim 5, wherein said detection unit includes two electrical contact points which are provided within said identification hole of said electrode connector and which are electrically connected to each other by said identification pin of said identifying connector when said idenification pin is inserted into the identification hole.

7. The apparatus according to claim 6, wherein said high-frequency power supply device includes a spray coagulation mode for performing spray coagulation capable of performing blood coagulation while generating a high voltage and electric discharge, while said instrument-side electrode is near but not in contact with the affected part of the living body.

8. The apparatus according to claim 1, wherein:

said detection means includes a detection unit for detecting connection of said leak current feedback cord; and said control means controls an output in at least a spray coagulation mode among said plurality of high-frequency output modes of said high-frequency power supply device, on the basis of a detection signal from said detection unit for detecting the connection of said leak current feedback cord.

9. The apparatus according to claim 8, wherein said control means forcibly prohibits use of the spray coagulation mode on the basis of the detection signal from said detection unit for detecting the connection of said leak current feedback cord.

10. The apparatus according to claim 8, wherein said control means forcibly prohibits use of the spray coagulation mode on the basis of the detection signal from said detection unit for detecting the connection of said leak current feedback cord, and lowers maximum output values in the other high-frequency output modes.

11. The apparatus according to claim 8, wherein said control means forcibly prohibits use of the spray coagulation mode on the basis of the detection signal from said detection unit for detecting the connection of said leak current feedback cord, and sets to a coagulation mode in which blood coagulation is performed at a lower voltage than in the spray coagulation.

12. A high-frequency cauterizing apparatus comprising:

a high-frequency power supply device, having a plurality of high-frequency output modes including a spray coagulation mode for performing spray coagulation capable of performing blood coagulation while generating a high voltage and electric discharge, for generating a high-frequency current;

a high-frequency medical treatment instrument, connected to said high-frequency power supply device, and comprising a living body-side electrode arranged to be put in contact with a living body and a medical instrument-side electrode arranged to be put in contact with an affected part of the living body;

an endoscope connected to said high-frequency power supply device and carrying said high-frequency medical treatment instrument;

a leak current feedback cord, electrically connected to a body portion of the endoscope, for connecting the body portion of the endoscope and said high-frequency power supply device;

means for equalizing a potential of the body portion of the endoscope to that of the living body-side electrode of said medical treatment instrument via said leak current feedback cord;

detection means for detecting a connection of said leak current feedback cord to said high-frequency power supply device; and control means for controlling an output in at least a spray coagulation mode among said plurality of high-frequency output modes of said high-frequency power supply device, on the basis of a detection signal from said detection means for detecting the connection of said leak current feedback cord to said high-frequency power supply device.

13. A high-frequency cauterizing apparatus comprising:

a high-frequency power supply device, having a plurality of high-frequency output modes, for generating a high-frequency current;

at least one medical treatment instrument to be connected to said high-frequency power supply device;

said at least one medical treatment instrument to be connected to said high-frequency power supply device comprising an endoscope and a high-frequency medical treatment instrument carried by said endoscope, said high-frequency medical treatment instrument having two electrodes, a living body-side electrode for performing a cauterizing treatment for a living body tissue by a high-frequency current produced by said high-frequency power supply device, said living body-side electrode being arranged to be put in contact with the living body, and a medical instrument-side electrode to be put in contact with an affected part of a living body;

detection means for detecting mechanical connection of said medical treatment instrument to said high-frequency power supply device;

control signal generating means for identifying the type of the medical treatment instrument responsive to a detection signal from said detection means, and for generating a control signal; and control means for controlling a high-frequency output from said high-frequency power supply device on the basis of said control signal generated from said control signal generating means; and said endoscope including a leak current feedback cord electrically connected to a body portion of said endoscope; and said high-frequency power supply device including means for equalizing a potential of the living body-side electrode of said high-frequency medical treatment instrument to that of the body portion of said endoscope via said leak current feedback cord.

14. The apparatus according to claim 13, wherein said high-frequency power supply device has a spray coagulation mode for performing spray coagulation capable of performing blood coagulation while generating a high voltage and electric discharge, while said instrument-side electrode is near but not in contact with the affected part of the living body.

15. The apparatus according to claim 14, wherein;

said detection means includes a detection unit for detecting connection of said leak current feedback cord; and said control means controls an output in at least a spray coagulation mode among said plurality of high-frequency output modes of said high-frequency power supply device, on the basis of a detection signal from said detection unit for detecting the connection of said leak current feedback cord.

16. The apparatus according to claim 15, wherein said control means forcibly prohibits use of the spray coagulation mode on the basis of the detection signal from said detection unit for detecting the connection of said leak current feedback cord.

17. The apparatus according to claim 15, wherein said control means forcibly prohibits use of the spray coagulation mode on the basis of the detection signal from said detection unit for detecting the connection of said leak current feedback cord, and lowers maximum output values in the other high-frequency output modes.

18. The apparatus according to claim 15, wherein said control means forcibly prohibits use of the spray coagulation mode on the basis of the detection signal from said detection unit for detecting the connection of said leak current feedback cord, and changes the spray coagulation mode to a coagulation mode in which blood coagulation is performed at a lower voltage than in the spray coagulation.

* * * * *